(12) United States Patent
Keith et al.

(10) Patent No.: US 9,278,199 B2
(45) Date of Patent: Mar. 8, 2016

(54) METHOD FOR TREATMENT OF ETHMOIDS

(75) Inventors: Peter T. Keith, Lanesboro, MN (US);
Theodore O. Truitt, St. Cloud, MN (US); Thomas V. Ressemann, St. Cloud, MN (US)

(73) Assignee: ENTELLUS MEDICAL, INC., Plymouth, MN (US)

( * ) Notice: Subject to any disclaimer, the term of this patent is extended or adjusted under 35 U.S.C. 154(b) by 71 days.

(21) Appl. No.: 13/555,007

(22) Filed: Jul. 20, 2012

(65) Prior Publication Data

US 2012/0283625 A1    Nov. 8, 2012

Related U.S. Application Data

(63) Continuation of application No. 11/696,936, filed on Apr. 5, 2007, now Pat. No. 8,241,266.

(51) Int. Cl.
*A61M 25/10* (2013.01)
*A61M 25/00* (2006.01)
*A61B 1/233* (2006.01)
*A61B 17/24* (2006.01)
*A61B 17/34* (2006.01)

(52) U.S. Cl.
CPC .......... *A61M 25/10* (2013.01); *A61M 25/0084* (2013.01); *A61B 1/233* (2013.01); *A61B 17/24* (2013.01); *A61B 17/3478* (2013.01); *A61M 2025/0089* (2013.01); *A61M 2025/0091* (2013.01); *A61M 2025/1093* (2013.01)

(58) Field of Classification Search
CPC ............. A61M 2025/0089; A61M 2025/0091; A61M 25/0084; A61M 25/10; A61M 2025/1093

USPC .......................................... 604/500, 506, 514
See application file for complete search history.

(56) References Cited

U.S. PATENT DOCUMENTS

| | | |
|---|---|---|
| 5,112,299 A | 5/1992 | Pascaloff |
| 5,490,860 A | 2/1996 | Middle et al. |
| 5,632,762 A | 5/1997 | Myler |
| 5,645,528 A | 7/1997 | Thome |
| 5,795,325 A | 8/1998 | Valley et al. |

(Continued)

FOREIGN PATENT DOCUMENTS

| | | |
|---|---|---|
| EP | 1598015 A1 | 11/2005 |
| WO | 2005/086945 A2 | 9/2005 |

OTHER PUBLICATIONS

PCT International Search Report for PCT/US08/59236, Applicant: Entellus Medical, Inc., Form PCT/ISA/210 and 220, dated Jun. 4, 2009 (3 pages).

(Continued)

*Primary Examiner* — Kevin C Sirmons
*Assistant Examiner* — Shefali Patel
(74) *Attorney, Agent, or Firm* — Vista IP Law Group

(57) ABSTRACT

A method of treating diseased ethmoid sinuses in a patient with a therapeutic agent includes providing an injection device comprising an elongate member having a proximal end, a distal tip or end, and a lumen extending between the distal tip or end and the proximal end, the proximal end being operatively coupled to a source of the therapeutic agent. The distal tip or end of the injection device is inserted at least partially within an interior portion of an ethmoid air cell. The therapeutic agent is then injected into the interior portion of the ethmoid air cell using the injection device, the therapeutic agent being delivered via the lumen in the elongate member.

6 Claims, 13 Drawing Sheets

(56) References Cited

U.S. PATENT DOCUMENTS

| | | | |
|---|---|---|---|
| 5,964,767 | A | 10/1999 | Tapia et al. |
| 6,543,452 | B1 | 4/2003 | Lavigne |
| 6,851,424 | B2 | 2/2005 | Scopton |
| 7,070,574 | B2 | 7/2006 | Jackson et al. |
| 7,520,876 | B2 | 4/2009 | Ressemann et al. |
| 7,678,099 | B2 | 3/2010 | Ressemann et al. |
| 7,842,062 | B2 | 11/2010 | Keith et al. |
| 7,879,061 | B2 | 2/2011 | Keith et al. |
| 7,918,871 | B2 | 4/2011 | Truitt et al. |
| 8,241,266 | B2 | 8/2012 | Keith et al. |
| 8,277,478 | B2 | 10/2012 | Drontle et al. |
| 8,282,667 | B2 | 10/2012 | Drontle et al. |
| 8,348,969 | B2 | 1/2013 | Keith et al. |
| 8,568,439 | B2 | 10/2013 | Keith et al. |
| 8,585,728 | B2 | 11/2013 | Keith et al. |
| 8,585,729 | B2 | 11/2013 | Keith et al. |
| 8,623,043 | B1 | 1/2014 | Keith et al. |
| 8,657,846 | B2 | 2/2014 | Keith et al. |
| 8,801,670 | B2 | 8/2014 | Drontle et al. |
| 8,834,513 | B2 | 9/2014 | Hanson et al. |
| 8,882,795 | B2 | 11/2014 | Drontle et al. |
| 8,888,686 | B2 | 11/2014 | Drontle et al. |
| 8,915,938 | B2 | 12/2014 | Keith et al. |
| 8,986,340 | B2 | 3/2015 | Drontle et al. |
| 9,005,284 | B2 | 4/2015 | Ressemann |
| 9,101,739 | B2 | 8/2015 | Lesch, Jr. et al. |
| 2002/0138121 | A1 | 9/2002 | Fox |
| 2003/0018299 | A1* | 1/2003 | Stone .................... 604/135 |
| 2004/0064150 | A1* | 4/2004 | Becker .................... 606/196 |
| 2004/0236313 | A1 | 11/2004 | Klein |
| 2005/0203489 | A1 | 9/2005 | Saadat et al. |
| 2005/0240147 | A1 | 10/2005 | Makower et al. |
| 2005/0245906 | A1* | 11/2005 | Makower ............. A61B 5/06 604/891.1 |
| 2006/0004286 | A1 | 1/2006 | Chang et al. |
| 2006/0004323 | A1 | 1/2006 | Chang et al. |
| 2006/0063973 | A1 | 3/2006 | Makower et al. |
| 2006/0095066 | A1 | 5/2006 | Chang et al. |
| 2006/0100687 | A1 | 5/2006 | Fahey et al. |
| 2006/0210605 | A1 | 9/2006 | Chang et al. |
| 2007/0005094 | A1 | 1/2007 | Eaton et al. |
| 2007/0073269 | A1 | 3/2007 | Becker |
| 2007/0250105 | A1 | 10/2007 | Ressemann et al. |
| 2008/0015472 | A1 | 1/2008 | Ressemann et al. |
| 2008/0015497 | A1 | 1/2008 | Keith et al. |
| 2008/0015544 | A1 | 1/2008 | Keith et al. |
| 2008/0015626 | A1 | 1/2008 | Keith et al. |
| 2008/0033353 | A1 | 2/2008 | Truitt et al. |
| 2008/0097239 | A1 | 4/2008 | Chang et al. |
| 2008/0172033 | A1 | 7/2008 | Keith et al. |
| 2009/0216196 | A1 | 8/2009 | Drontle et al. |
| 2010/0211007 | A1 | 8/2010 | Lesch, Jr. et al. |
| 2010/0274222 | A1 | 10/2010 | Setliff, III et al. |
| 2011/0071349 | A1 | 3/2011 | Drontle et al. |
| 2011/0224652 | A1 | 9/2011 | Drontle et al. |
| 2011/0264134 | A1 | 10/2011 | Drontle et al. |
| 2012/0010646 | A1 | 1/2012 | Keith et al. |
| 2012/0071727 | A1 | 3/2012 | Hanson et al. |
| 2013/0030458 | A1 | 1/2013 | Drontle et al. |
| 2013/0030459 | A1 | 1/2013 | Drontle et al. |
| 2013/0041463 | A1 | 2/2013 | Ressemann |
| 2013/0072958 | A1 | 3/2013 | Ressemann et al. |
| 2013/0123833 | A1 | 5/2013 | Lesch et al. |
| 2014/0350520 | A1 | 11/2014 | Drontle et al. |
| 2014/0357959 | A1 | 12/2014 | Hanson et al. |
| 2014/0364700 | A1 | 12/2014 | Hanson et al. |
| 2014/0378776 | A1 | 12/2014 | Hanson et al. |
| 2015/0031950 | A1 | 1/2015 | Drontle et al. |
| 2015/0045827 | A1 | 2/2015 | Drontle et al. |
| 2015/0105818 | A1 | 4/2015 | Keith et al. |

OTHER PUBLICATIONS

PCT Written Opinion of the International Search Authority for PCT/US08/59236, Applicant: Entellus Medical, Inc., Form PCT/ISA/237, dated Jun. 4, 2009 (4 pages).

PCT International Preliminary Report on Patentability (Chapter I of the Patent Cooperation Treaty) for PCT/US2008/059236, Applicant: Entellus Medical, Inc., Form PCT/IB/326 and 373, facsimile date Feb. 23, 2010 (8 pages).

Folweiler, David S., Nasal Specific Technique as Part of a Chiropractic Approach to Chronic Sinusitis and Sinus Headaches, Journal of Manipulative and Physiological Therapeutics, vol. 18, No. 1, (Jan. 1995).

Entellus Medical, 510(k) Premarket Notification cover letter and Attachment B: Predicate Device Labeling, dated Aug. 15, 2007.

Lavigne, F., et al., "Selective Irrigation of the Sinuses in the Management of Chronic Rhinosinusitis Refractory to Medical Therapy: A Promising Start," The Journal of Otolaryngology, vol. 33, Nov. 1, 2004, pp. 10-16.

PCT International Search Report for PCT/US07/66187, Applicant: Entellus Medical, Inc., Form PCT/ISA/210 and 220, dated Apr. 17, 2008 (5 pages).

PCT Written Opinion of the International Search Authority for PCT/US07/66187, Applicant: Entellus Medical, Inc., Form PCT/ISA/237, dated Apr. 17, 2008 (5 pages).

International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2008 (4 pages).

PCT International Search Report for PCT/US07/088834, Applicant: Entellus Medical, Inc., Form PCT/ISA/210 and 220, dated May 20, 2008 (4 pages).

PCT Written Opinion of the International Search Authority for PCT/US07/088834, Applicant: Entellus Medical, Inc., Form PCT/ISA/237, dated May 20, 2008 (10 pages).

International Preliminary Report on Patentability (Chapter I of the Patent Cooperation Treaty) of the International Bureau for PCT/US2007/088834, Applicant: Entellus Medical, Inc., Form PCT/IB/326, dated Jul. 30, 2009 (9 pages).

\* cited by examiner

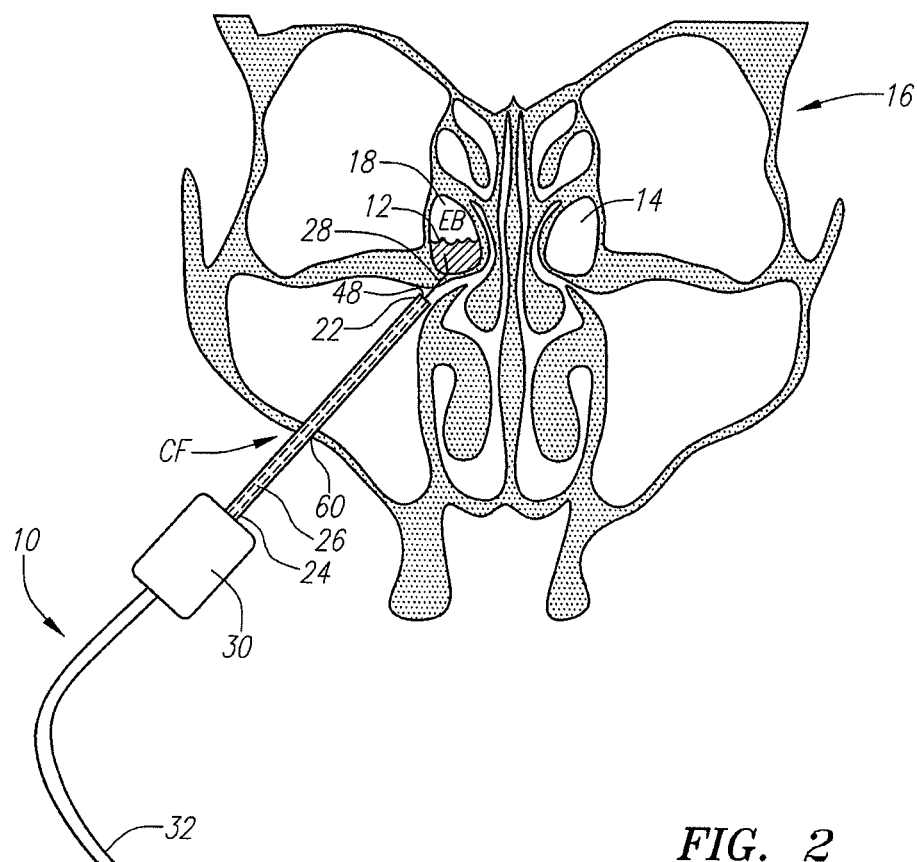
FIG. 2
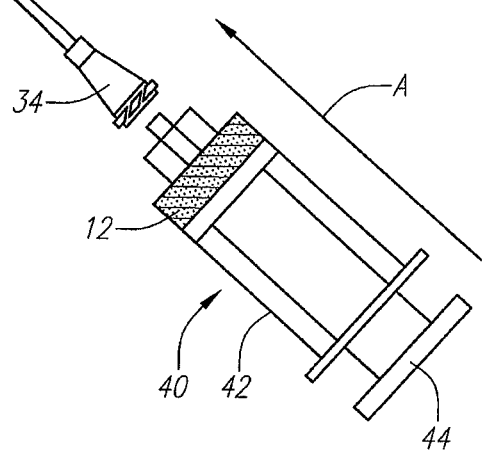

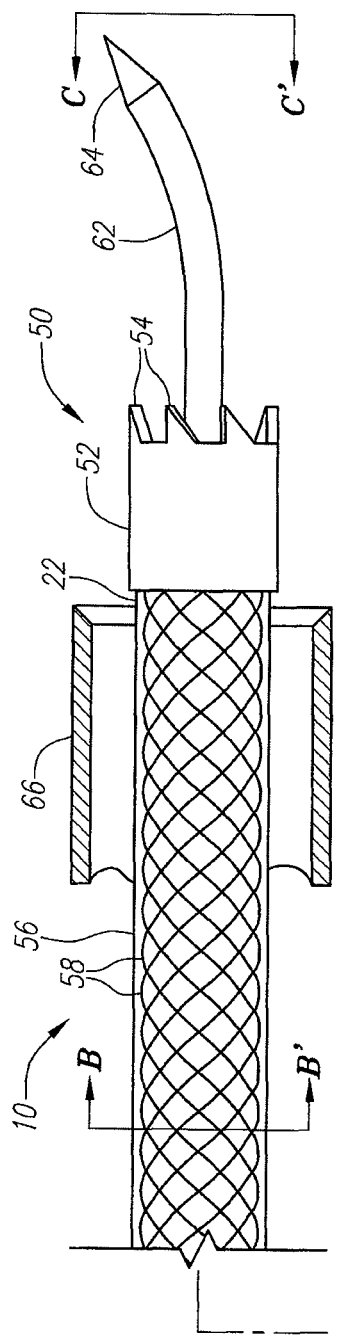
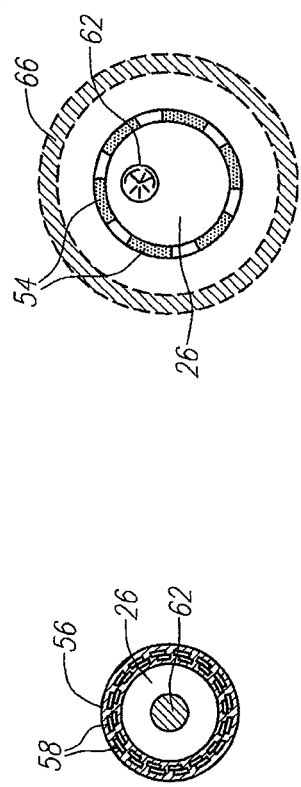
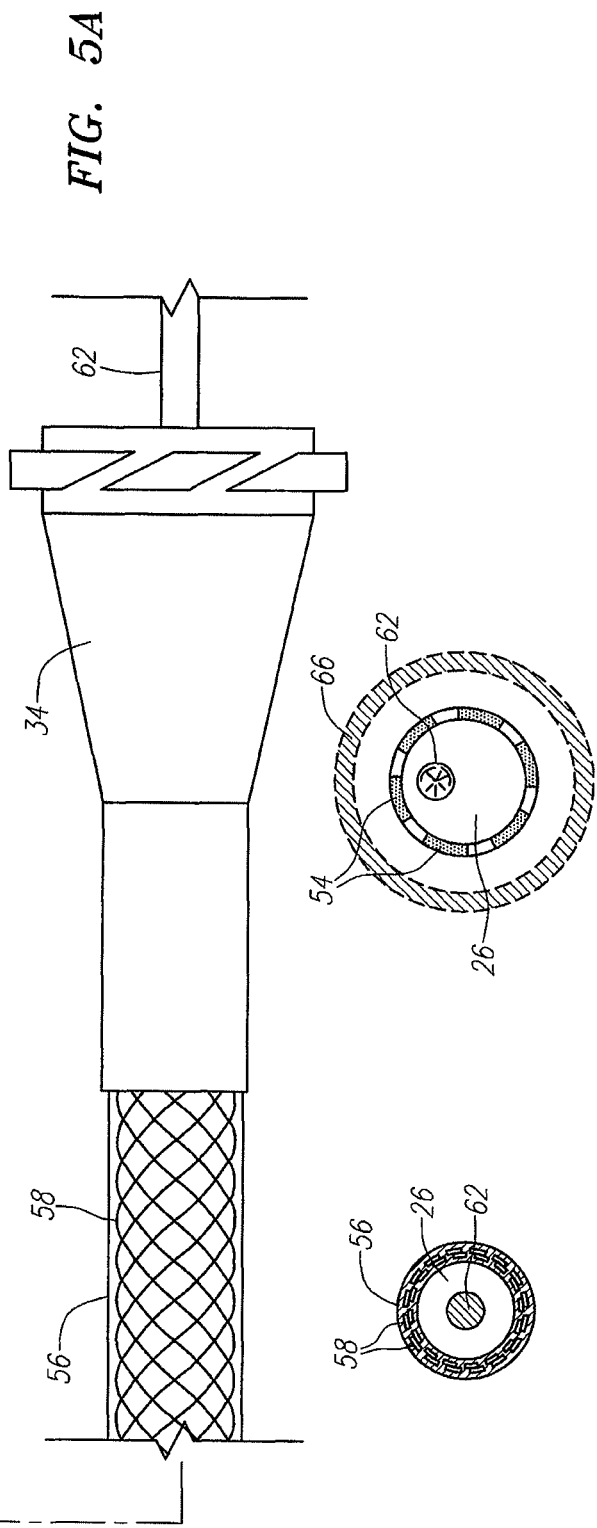
FIG. 5A
FIG. 5B
FIG. 5C

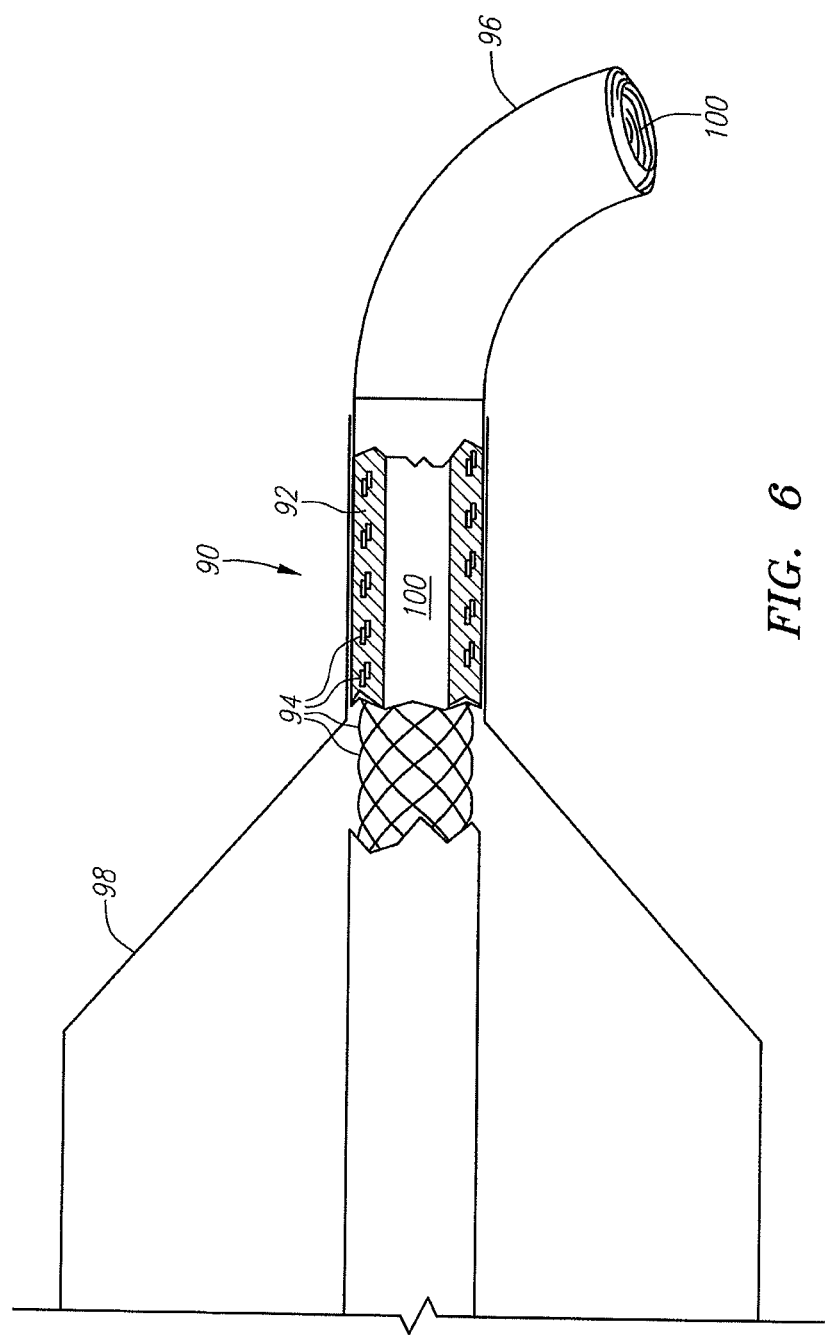

METHOD FOR TREATMENT OF ETHMOIDS

RELATED APPLICATION

This application is a continuation of U.S. patent application Ser. No. 11/696,936 filed on Apr. 5, 2007, now issued as U.S. Patent No. 8,241 266, the entire disclosure of which is expressly incorporated by reference herein.

FIELD OF THE INVENTION

The field of the invention generally relates to devices and methods for the treatment or amelioration of sinusitis. More specifically, the field of the invention relates to the treatment of disease of the ethmoids.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has an opening into the nasal passage called an ostium. When the mucosa of one or more of the ostia or regions near the ostia become inflamed, the egress of mucous is interrupted, setting the stage for an infection of the sinus cavity, i.e., sinusitis. Infections of the maxillary and/or ethmoid sinuses make up the vast majority of cases of sinusitis, with far fewer cases involving the sphenoids and frontals.

Unlike the maxillary, frontal, and sphenoid sinuses, the ethmoid sinuses are comprised of several individual air cells, each of which has a relatively small drainage path and ostium for drainage into the nasal cavity. The ethmoid sinuses are grouped into anterior and posterior air cells. The anterior air cells are anterior to the basal lamella of the middle turbinate while the posterior air cells are posterior to the basal lamella. From a sinusitis standpoint, the anterior air cells are usually isolated from the posterior air cells, and more commonly involved with sinusitis.

It is estimated that about 25-30% of sinus disease is confined to the maxillary sinuses. Another 20-30% of sinus disease, however, further involves the anterior ethmoid sinus air cells, the largest (and most commonly involved) of which is typically the ethmoid bulla. Currently, the surgical treatment of disease of the ethmoids is accomplished by ethmoidectomy during functional endoscopic sinus surgery (FESS). In this process, the walls of the air cells are essentially completely removed to their lateral aspect, essentially eliminating them. While this procedure is relatively simple for a surgeon, the patient is almost always under general anesthesia. Furthermore, there is a significant amount of post-surgery pain during recovery for the patient when ethmoidectomy (and any additional surgery done during FESS) is performed. There thus is a need for less invasive ways to treat diseased ethmoid sinuses.

While it is potentially possible to address disease of the involved ethmoid air cells less invasively by improving their natural drainage, such as by balloon dilation, the location of the individual ostia are quite variable, and they are difficult to find with any currently available visualization techniques. While a certain percentage of patients in whom some or all of their anterior ethmoid air cells are diseased, in addition to their maxillary sinuses and associated osteo meatal units (OMU) including their ostia and infundibular spaces, treatment of only their OMU by dilation of the maxillary ostia and remodeling of the uncinate process may also resolve any disease of the anterior ethmoid air cells. However, in some patients with both anterior ethmoid and maxillary disease, it may be necessary to directly intervene on one or more of the anterior air cells, such as the ethmoid bulla. Ideally such an intervention would be minimally invasive, and could be performed under local anesthesia, without requiring general anesthesia. Such a procedure, in addition to the previously described dilation treatments for other sinuses such as maxillary, frontal, and sphenoid, has the potential to be performed in a physician's office or on an outpatient basis. This would be especially true if the procedure could be performed using endoscopic techniques.

For these and other reasons, there is a clear need for better methods and devices for the treatment of diseased ethmoid sinuses.

SUMMARY

In a first aspect of the invention, a method of treating diseased ethmoid sinuses in a patient with a therapeutic agent includes providing an injection device comprising an elongate member having a proximal end, a distal tip or end, and a lumen extending between the distal tip and the proximal end, the proximal end being operatively coupled to a source of the therapeutic agent. The distal tip of the injection device is inserted at least partially within an interior portion of an ethmoid air cell. The therapeutic agent is then injected into the interior portion of the ethmoid air cell using the injection device, the therapeutic agent being delivered via the lumen in the elongate member.

In a second aspect of the invention, a method of treating diseased ethmoid sinuses in a patient with a therapeutic agent includes providing an injection device having an elongate member having a proximal end, a distal end having a cutting element, and a lumen extending between the distal tip and the proximal end, the proximal end being operatively coupled to a source of the therapeutic agent. The injection device is advanced so as to place the distal tip adjacent to a wall of an ethmoid air cell. A passageway is then formed in an ethmoid air cell by rotating the cutting element against the wall of the ethmoid air cell. A therapeutic agent is then injected into the interior portion of the ethmoid air cell. The passageway may be further expanded, such as by dilation.

In another aspect of the invention, a method of treating diseased ethmoid sinuses in a patient with a therapeutic agent includes providing a delivery device having an elongate member having a proximal end, a distal end, and a lumen extending between the distal end and the proximal end, the proximal end being operatively coupled to a source of the therapeutic agent. The distal end of the elongate member is advanced adjacent and external to an ethmoid air cell. The therapeutic agent is then delivered to an external surface (e.g., wall) of the ethmoid air cell.

BRIEF DESCRIPTION OF THE DRAWINGS

FIG. 1 illustrates the trans-nasal placement of the delivery device.

FIG. 2 illustrates a cross-sectional view of the sinus cavities of a patient illustrating the delivery of a therapeutic agent to an ethmoid air cell via an injection device according to another embodiment. The injection device includes an elongate piercing member and a syringe. FIG. 2 illustrates the placement of the delivery device via an access passageway formed in the canine fossa region of the patient.

FIG. 5A illustrates a side view of a drilling device according to one embodiment of the invention. The drilling device includes a proximal hub and a distally located cutting head. Optional centering wire/centering tube are also illustrated.

FIG. 5B illustrates a cross-sectional view of the drilling device taken along the line B'-B of FIG. 5A.

FIG. 5C illustrates a cross-sectional view of the drilling device taken along the line C'-C of FIG. 5A.

FIG. 6 illustrates a distal end of a balloon dilation catheter. A portion of the balloon dilation catheter is shown in cross-section along with another segment illustrating the incorporated braid structure.

DETAILED DESCRIPTION

Figure 1:
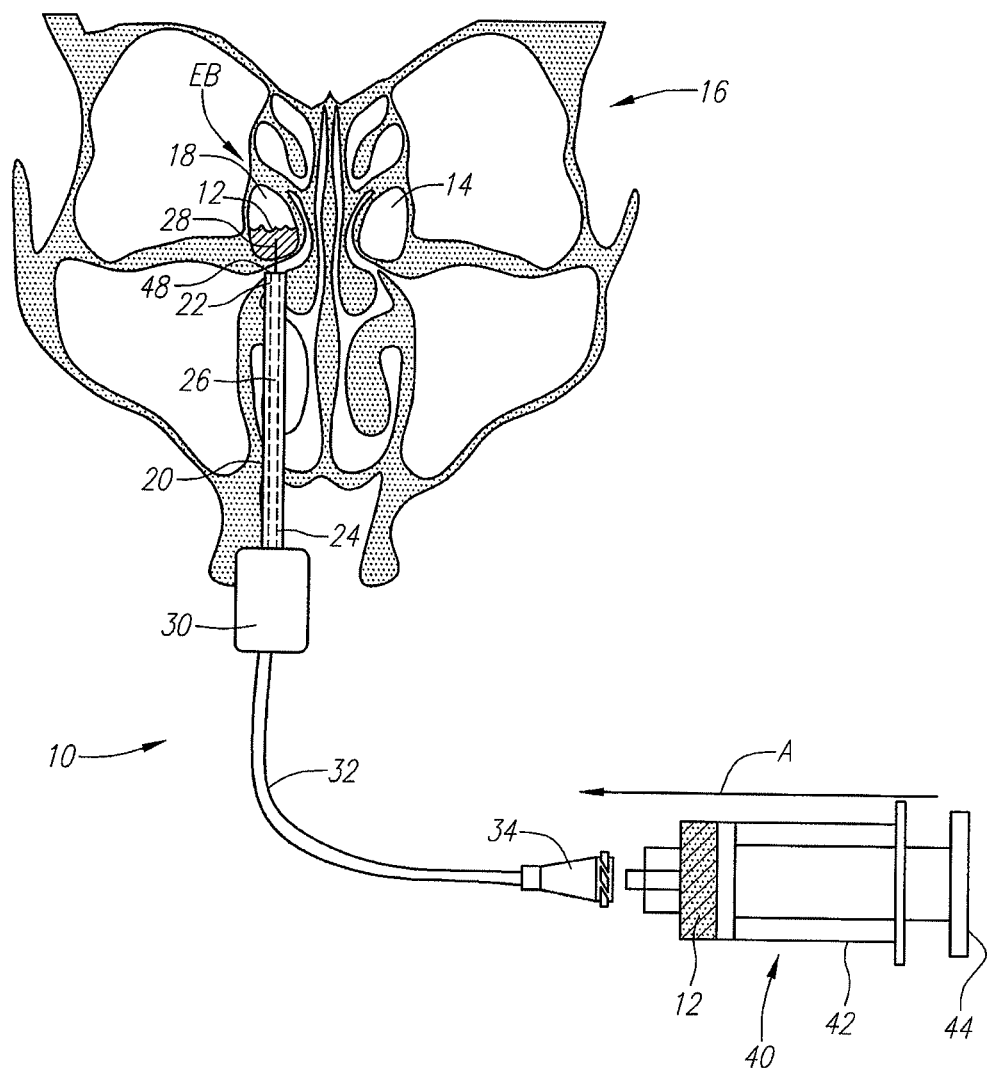
FIG. 1 illustrates a cross-sectional view of the sinus cavities of a patient illustrating the delivery of a therapeutic agent to an ethmoid air cell via an injection device. The injection device includes an elongate piercing member and a syringe.

FIG. 1 illustrates an injection or delivery device 10 that is used to deliver a therapeutic agent 12 into an ethmoid sinus 14 of a patient 16. As illustrated in FIG. 1, the injection device 10 is used to deliver the therapeutic agent 12 into the interior space of an ethmoid air cell 18. FIG. 1 illustrates therapeutic agent 12 being delivered to the ethmoid bulla (EB) although other ethmoid air cells 18 may also be treated in accordance with the invention. In still other embodiments, however, the delivery device 10 may be used to apply the therapeutic agent 12 onto an exterior surface of an ethmoid air cell 18. For example, the therapeutic agent 12 may be applied to a wall of an ethmoid air cell 18. FIG. 1. illustrates the injection device 10 delivering a therapeutic agent 12 via a transnasal route. As explained herein in more detail, the injection device 10 may be delivered directly into a sinus cavity via an artificially created passageway formed in, for example, the canine fossa CF region.

As seen in FIG. 1, the injection device 10 generally is formed from an elongate member 20 having a distal end 22 and a proximal end 24 and at least one lumen 26 passing between the distal and proximal ends 22, 24. The injection device 10 may include a sharpened tip or needle 28 as illustrated in FIG. 1. Of course, the sharpened tip or needle 28 would include a lumen (not shown in FIG. 1) in communication with elongate member 20 to permit the passage of the therapeutic agent 12. The elongate member 20 may be formed from a polymer or plastic-based material that provides flexibility as well as good pushability during the injection process. In another aspect, the elongate member 20 may be formed from a metallic material. For example, the elongate member 20 may include an injection needle 20 having a smaller diameter, sharpened hypodermic needle 28 located at the distal end 22. The elongate member 20 should have sufficient columnar strength such during puncturing or advancement of the tip 28 through the ethmoid air cell 18, the elongate member 20 does not buckle. To aid in this regard, one or more supporting structures such as braids, coils, jackets and the like may be incorporated into one or more portions of the elongate member 20.

The elongate member 20 may have a handle or grip 30 that the physician uses to grasp the device 10. The handle or grip 30 may include a flexible connector 32 having a lumen therein that terminates at a proximal hub 34. The proximal hub 34 may include a Luer fitting or the like. As seen in FIG. 1, the device 10 is operatively coupled to a source of therapeutic agent 12 that is contained in a dispensing device 40. The dispensing device 40 may include a syringe having a barrel 42 along with a moveable plunger 44. When the dispensing device 40 is coupled to proximal hub 34 and the plunger 44 is depressed in the direction of arrow A, therapeutic agent 12 contained in the barrel 42 is forced into the lumen 26 of the injection device. The therapeutic agent 12 then exits the distal tip 22 (e.g., needle or sharpened tip 28) and enters the interior of the ethmoid air cell 18.

While FIG. 1 illustrates a needle 28 that is disposed at the distal end 22 of the elongate member 20 it should be understood that the needle 28 is optional. For example, in one alternative configuration, the distal end 22 of the elongate member 20 may be sharpened or pointed to aid in penetrating the ethmoid air cells 18. Still referring to FIG. 1, a shoulder or flange 48 may be formed at a distal end 22 of the elongate member 20. The shoulder or flange 48 has a larger effective cross-sectional area or diameter than the needle 28 so as to prevent additional advancement of the needle 28 into the ethmoid air cell 18. The shoulder or flange 48 is thus a safety feature that prevents the needle 28 from being inserted too far into the ethmoid air cell 18.

The therapeutic agent 12 may be delivered in a fluid or fluid-like state having a range of viscosities. For example, the therapeutic agent 12 may be in liquid, gel, cream, paste, or other such forms as available to the physician. The therapeutic agent 12 may be any class of agent that targets inflammation, infection, either viral, bacterial, or fungal (e.g., fungicide). The therapeutic agent 12 may also include a mucosal agent (e.g., affecting mucous viscosity), an expectorant, a secretagogue (e.g., Mucinex® (guaifenesin)), a polyposis agent, a scarring agent, or the like. Two preferred class of agents are anti-inflammatories such as steroids (e.g. Kenalog® (triamcinolone), dexamethasone), antibiotics (e.g. Cipro® (ciprofloxacin), tobramycin, neomycin, gentamicin, ofloxicin), or a combination of the two (e.g. Ciprodex® (ciprofloxacin/dexamethasone), Tobradex® (tobramycin/dexamethasone), Cortisporin (Neomycin/Polymyxin B/hydrocortisone)). Other possible agents would include an antifungal (e.g. Amphotericin B) and bacteriostatic agents (e.g. methylene blue and gentian violet). Any combination of agents may be applied, which may either be pre-mixed within the device 10, or serially within the target site. The therapeutic agents 12 may be modified prior to application, such as by dilution (e.g., in saline), concentration, modification to pH (e.g. by adding a buffering agent). Also, additional therapeutic agents 12 may be added, such as, for instance, an anesthetic like lidocaine, tetracaine, Pontocaine® (tetracaine), benzocaine, cocaine, or the like. Additionally vasoconstrictive agents such as epinephrine or Afrin® (oxymetazoline hydrochloride) could be added to the therapeutic agent 12 to be applied. Finally, for visualization purposes, a radiographic contrast may be added to the agent to facilitate visualization with fluoroscopy.

FIG. 2 illustrates an injection device 10 similar to that illustrated in FIG. 1 that is advanced via an artificial passageway 60 formed in the canine fossa CF region of the patient 16. The artificial passageway 60 may be formed using a sharpened tool or the like (not shown) that pierces or punctures the thin structure of canine fossa CF. For example, a trocar, drill, needle, or piercing tool like that disclosed in U.S. patent application Ser. Nos. 11,379,691 and 11/623,740 may be used. The '691 and '740 Applications are incorporated herein by reference as if set forth fully herein. FIG. 2 illustrates an injection device 10 that is used to directly inject a therapeutic agent 12 into the ethmoid bulla EB. Of course, other ethmoid air cells 18 may be accessed in the same manner.

The injection of the therapeutic agent 12 may be done as a sole therapy that is directed specifically to the ethmoid sinuses 14 or, alternatively, therapeutic agent 12 may be delivered in conjunction with other interventional procedures performed in other non-ethmoid sinuses. For example, application of the therapeutic agent 12 may be performed either before or after dilation of one or more anatomical features (e.g., maxillary ostium, infundibulum, etc.) using the same or a separate interventional device. For example, a separate balloon catheter (not shown in FIG. 2) may be used to first dilate the maxillary ostium. Afterwards, the injection device 10 may be advanced through the same artificial passageway 60 formed in the canine fossa CF to deliver the therapeutic agent 12.

As seen in FIG. 2, the needle 28 positioned at the distal end 22 of the elongate member 20 may be bent or curved to aid in traversing the wall of the ethmoid air cell 18. The bend or curve in the needle 28 may be needed because of the trajectory of the injection device 10 during advancement via the canine fossa CF approach. Once the needle 28 is positioned within the interior of the ethmoid air cell 18, the therapeutic agent may be infused by depressing the plunger 44 of the coupled dispensing device 40. In this embodiment, the injection device 10 is preferably stiff enough on the distal end to pass into the interior of the ethmoid air cell 18 but flexible enough to facilitate handling and manipulation on the proximal end.

Figure 3:
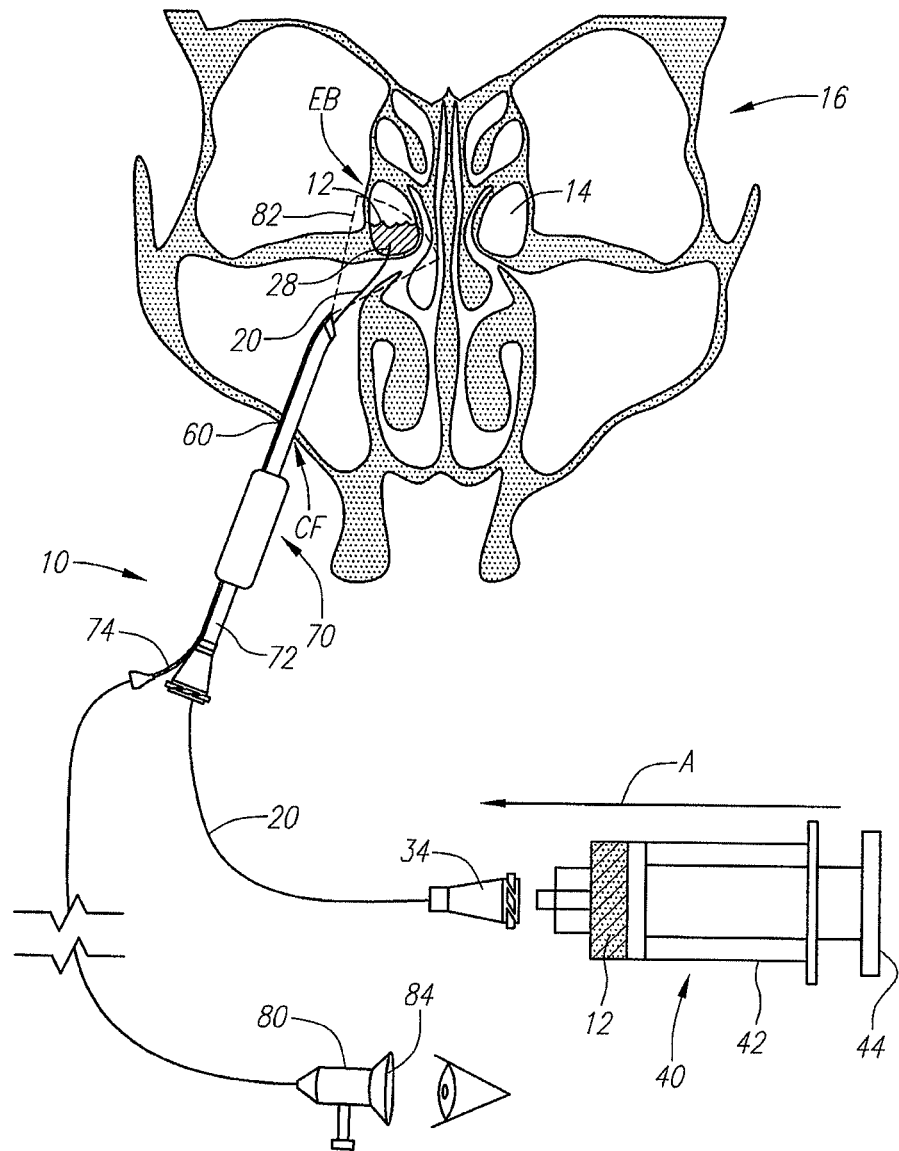
FIG. 3 illustrates a cross-sectional view of the sinus cavities of a patient illustrating the delivery of a therapeutic agent to an ethmoid air cell via an injection device according to another embodiment. The device includes a cannula through which the injection device passes. An imaging device is also illustrated disposed in the cannula.

FIG. 3 illustrates another embodiment of an injection device 10 that is used to directly inject a therapeutic agent 12 into an ethmoid air cell 18 via the canine fossa CF approach. In this embodiment, a cannula 70 is placed in the artificial passageway 60 formed in the canine fossa CF region. The cannula 70 may include multiple lumens for passage of various tools and devices. As shown in FIG. 3, the cannula 70 includes a first lumen or passageway 72 for passage of the elongate member 20 that is used to pierce the wall of the ethmoid air cell 18. A second lumen 74 is provided in the cannula 74 that is dimensioned to permit advancement and retraction of a visualization tool 80. For example, the visualization tool 80 may include an endoscope as illustrated in FIG. 3. The visualization tool 80 permits the physician to visualize a field of view 82 to better position and insert the injection device 10 into the ethmoid air cell 18. The endoscope 80 may include a eyepiece 84 or it may be coupled to a camera that may then display the image on a monitor (not shown). For example, the maxillary ostium and wall of the ethmoid bulla EB may be visualized to aid in placing the needle or tip 28 of the injection device 10 against the ethmoid wall of interest. Various cannulas 70 that may be used with this method are found in the '691 and '740 Applications which are incorporated be reference herein.

Prior to advancing the injection device 10 across the wall of the ethmoid air cell 18, a topical anesthesia can be sprayed, painted, or effused onto the area around the maxillary sinus ostium, uncinate process, and ethmoid bulla. Generally, the beating action of the cilia of the mucosa will naturally bring the anesthesia into the infundibulum and the surface of the ethmoid bulla EB. The topical anesthetic may be introduced through the same cannula 70.

Figure 4:
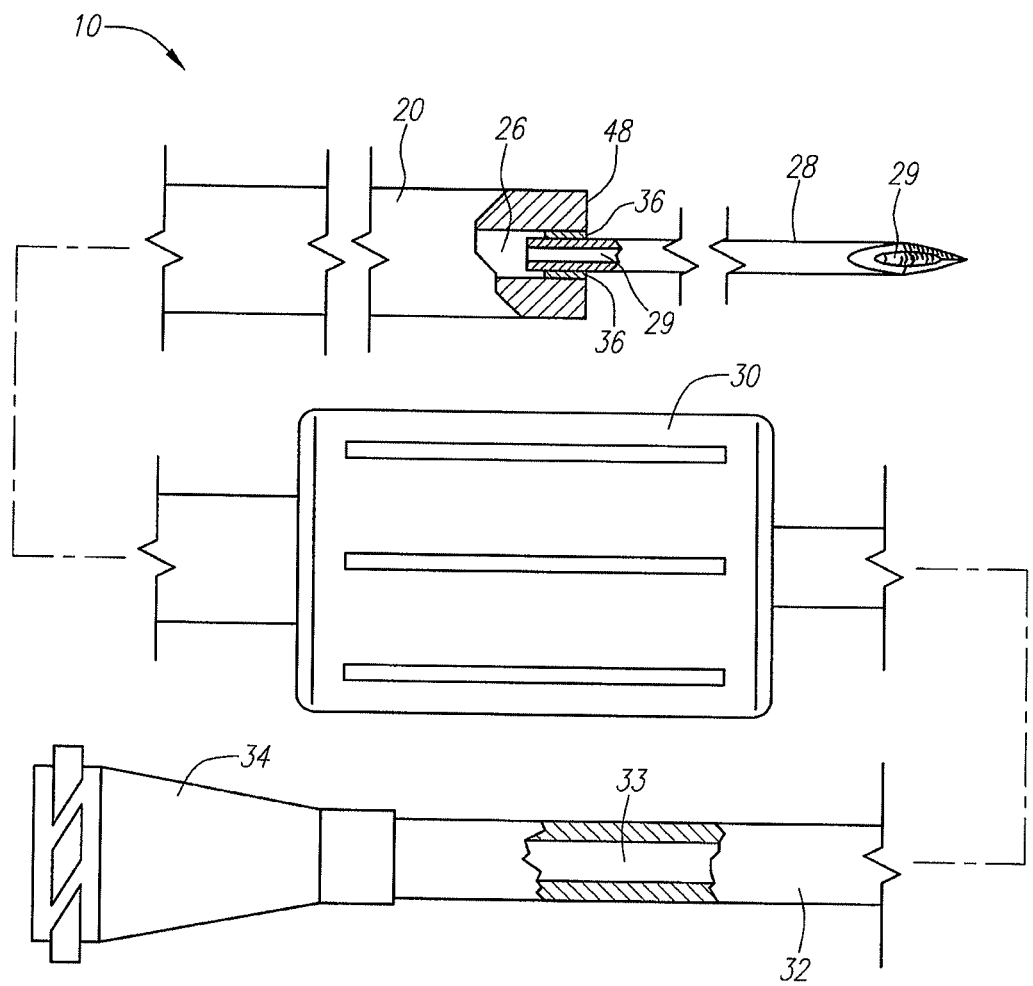
FIG. 4 illustrates a portion of an injection device according to one embodiment. The device includes an elongate member having a sharpened distal tip and a proximal portion. A central lumen passes through the proximal portion and distal tip for passage of the therapeutic agent.

FIG. 4 illustrates an injection device 10 according to one preferred embodiment. The injection device 10 of FIG. 4 may comprise an elongate member 20 in the form of a hollow needle or tube. A distal needle 28 is secured to the elongate member 20 and has a relatively small diameter, for example, from around 14 gauge to around 25 gauge and a length between about 1 mm to about 10 mm. The distal needle 28 includes a lumen 29 that communicates with the lumen 26 of the elongate member 20. The proximal section of the elongate member 20 has a larger diameter, for example, between about 0.005 inches to about 0.1 inches. The transition between the larger proximal elongate member 20 and the smaller distal needle 28 may form a shoulder or flange 48 that limits the depth of penetration of the distal needle 28 as explained above. The distal needle 28 may be bonded to the proximal elongate member 20 via a bond 36 such as a weld, adhesive, or the like. Alternatively, the distal needle 28 may be integrated into the proximal elongate member 20 in a one-piece configuration.

With reference to FIG. 4, the elongate member 20 may be constructed to be relatively stiff by virtue of the materials used or the diameter. The device 10 may include an optional handle 30 to facilitate handling and positioning of the injection device 10. The flexible connector 32 may also be optionally incorporated for ergonomics. As seen in FIG. 4, the flexible connector tube 32 includes a lumen 33 that communicates with the main lumen 26 of the elongate member 20. The proximal end of the flexible connector 32 terminates in a hub 34 such as, for instance, a Luer fitting.

The needle 28 may have a number of configurations. For example, the needle 28 may be straight as illustrated in FIG. 4 or, alternatively, the needle 28 may include a bend or curve as shown, for instance, in FIG. 2. In yet another alternative, the needle 28 and/or elongate member 20 may be manipulated or formed into the desired shape by the physician.

FIGS. 5A-5C illustrate an embodiment of an injection device 10 according to another embodiment. In this embodiment, the injection device includes an elongate member 20 having a lumen 26 therein for passage of the therapeutic agent 12. The distal end 22 of the elongate member 20 includes a cutting element 50. The cutting element 50 may include cutting head 52 that has a plurality of cutting surfaces 54 disposed about the periphery of the cutting head 52. The cutting surfaces 54 may include cutting blades, projections, abrasive or serrated elements that may be arranged in a circular or other pattern about the cutting head 52. FIGS. 5A and 5C illustrate a plurality of cutting blades 54 disposed about the cutting head 52.

As seen in FIGS. 5A and 5B, the elongate member 20 may comprise a torquable shaft 56 that is attached to and extends proximally from the cutting head 52. The torquable shaft 56 may be fabricated as a tube that incorporates a braid 58 or other torsionally rigid structure disposed within the shaft 56. Rotation of the torquable shaft 56 rotates the cutting head 52 along with the cutting surfaces 54. When the cutting surfaces 54 are pressed against the wall of the ethmoid air cell 18 and the torquable shaft 56 is rotated, a hole or passageway is formed in the air cell 18. As seen in FIG. 5A, the proximal end of the torquable shaft 56 may contain a hub 34 such as a Luer fitting. In this regard, the hub 34 may be secured to the dispensing device for injecting therapeutic agent 12 into the newly formed passage in the ethmoid air cell 18.

Still referring to FIGS. 5A-5C, the injection device 10 may include an optional centering device such as a centering wire 62. The centering wire 62 is dimensioned to fit within the lumen 26 of the torquable shaft 56 and includes a sharp or pointed distal tip 64. The tip 64 allows the centering wire 62 to "dig into" or penetrate the exterior mucosal tissue of the ethmoid air cell 18 and thus secure the position of the cutting element 50 for cutting through the wall of the ethmoid air cell 18. Depending on the angle of approach to the ethmoid air cell 18 (e.g., canine fossa CF or transnasal approach) and the geometry of the ethmoid air cell 18, an optional curve on the distal tip 64 of the centering wire 62 may be incorporated. The centering wire 62 is preferably removed from the elongate member 20 prior to infusion of the therapeutic agent 12. Of course, in another alternative aspect, the centering wire 62 may remain in place during infusion of the therapeutic agent 12. Alternatively, the centering device may include a centering tube 66 (shown in FIGS. 5A and 5C) which is disposed coaxially around the elongate member 20. The centering tube 66 may be moveably along the length of the elongate member 20 and cutting head 52 to provide a contact surface against the tissue or anatomical surface that is to be cut. This configuration of the centering device may be advantageous because, unlike the centering wire 62, there is no need to remove the tube 66 prior to infusion of the therapeutic agent 12.

The injection device 10 of FIGS. 5A-5C may be referred to as a drilling device 10 and may be sized to make a relatively small hole (e.g., having a diameter between about 0.5 mm and about 2 mm). For example, the drilling device 10 may take the form of a rotatable or torquable catheter with cutting capability (e.g., a drilling catheter). This may be adequate for subsequent infusion of the therapeutic agent 12. Furthermore, this may also facilitate some drainage and ventilation of the ethmoid air cell 18. However, drainage and ventilation of the ethmoid air cell 18 may necessitate a larger hole (e.g., larger than 2.0 mm). A larger hole or passageway may be accomplished by a larger drilling device, or a standard microdebrider, or a subsequent dilation with a dilation balloon catheter (not shown), following drilling of a relatively small hole.

FIG. 6 illustrates a delivery device 90 that is used to deliver a therapeutic agent 12 onto an exterior surface of an ethmoid air cell 18. Unlike the embodiments discussed above, this embodiment delivers the therapeutic agent 12 onto the exterior (e.g., wall) of the ethmoid air cell 18. There is no injection into an interior portion of an ethmoid air cell 18. The delivery device 90 of FIG. 6 includes an elongate member 92 such as a shaft which may incorporate a braided structure 94 to facilitate torque transfer to a distal tip 96 of the device 90. The distal tip 96 may be straight or curved as illustrated in FIG. 6. In addition, in another aspect of this embodiment, the shape of the distal tip 96 may be pre-formed, for example, by the physician prior to use.

FIG. 6 illustrates a distal region of the delivery device 90 and illustrates an optional expandable balloon 98. The presence of the balloon 98 is preferred if the device 90 is to be used for dilation of the maxillary ostium and infundibulum via the canine fossa CF. The balloon 98 may be expanded by the delivery of a fluid via a separate lumen (not shown) in the manner disclosed in the '691 and '740 Applications. The elongate member 92 includes a lumen 100 which is used to deliver the therapeutic agent 12. The proximal end of the elongate member 92 may include a hub (not shown) much like the prior embodiments which can then be secured to a dispensing device.

Figure 7:
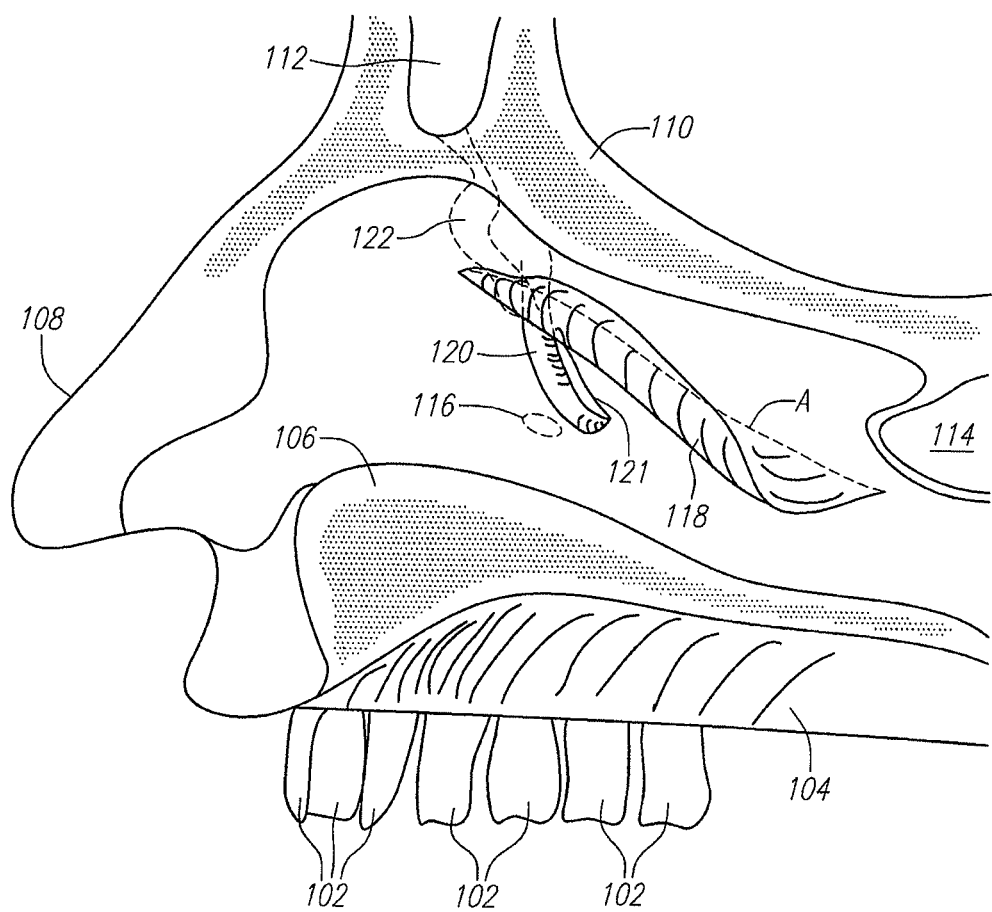
FIG. 7 illustrates a sagittal cross-sectional view of a portion of a patient's skull illustrating various anatomical features of the nasal cavity. The middle turbinate is lifted to reveal, among other structures, the uncinate process.

FIG. 7 generally illustrates the teeth 102, roof of the mouth 104, the palate 106, the nose 108, portions of the skull 110, the lower part of the right frontal sinus cavity 112, and a portion of the right sphenoid sinus cavity 114. The dotted circular line 116 is the ostium of the right maxillary sinus, which sits in a structure lateral to the nasal wall, and is thus hidden from view. The flap-like structure 118 is the middle turbinate. The middle turbinate 118 is shown being "lifted up" which reveals the uncinate process 120. Lateral to the uncinate process 120 is a slot-like space of the infundibulum 121, which is lateral to the uncinate process 120. The channel or frontal drainage 122 (shown as a dashed line going in the superior or vertical direction) going up to the right frontal 112 sinus is also depicted, as it is lateral to the nasal wall. The dashed line A just above the middle turbinate 118 depicts the site of attachment (shown as attached to the nasal wall but this can vary in different patients).

Figure 8:
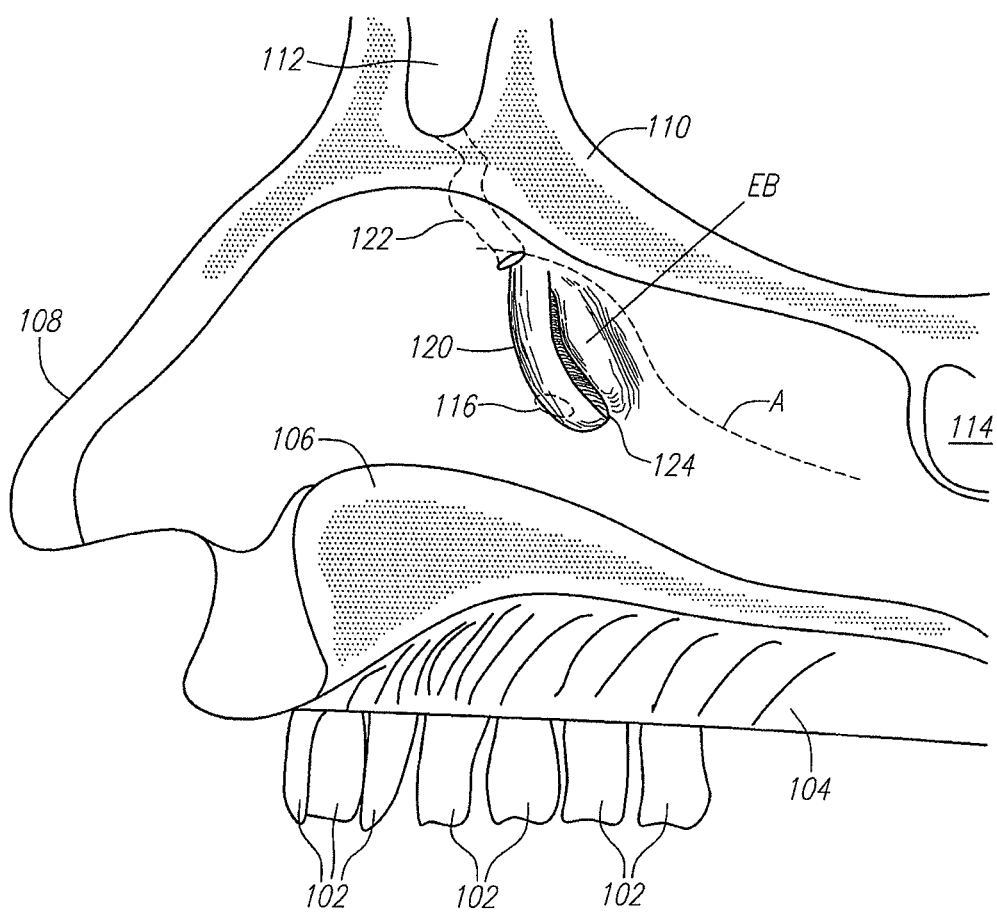
FIG. 8 illustrates a sagittal cross-sectional view of a portion of a patient's skull like that shown in FIG. 7 with the middle turbinate removed.

FIG. 8 illustrates various anatomical structures of the nasal cavity that are located "underneath" or lateral to the middle turbinate 118. For illustration purposes, the middle turbinate 118 in FIG. 7 has been removed to reveal the uncinate process 120 which is a rim of mucosa covered bone extending medially from the lateral nasal wall and it is anterior to the hiatus semilunaris 124, the opening between the edge of the uncinate process 120 and the more posterior ethmoid bulla EB that appears to be bulged outward. The "pocket" underneath or lateral to the uncinate process 120 is the ethmoid infundibulum 121. The ethmoid infundibulum 121 as well as the ostium 116 and the hiatus semilunaris 124 associated with the maxillary sinus can all be quite narrowed in a patient with suspected sinusitis. This narrowing can be a combination of inflammation of the mucosa, edema, scar tissue, mucous, pus, polypoid tissue, narrowed underlying bony structure, or other pathology.

Figure 9:
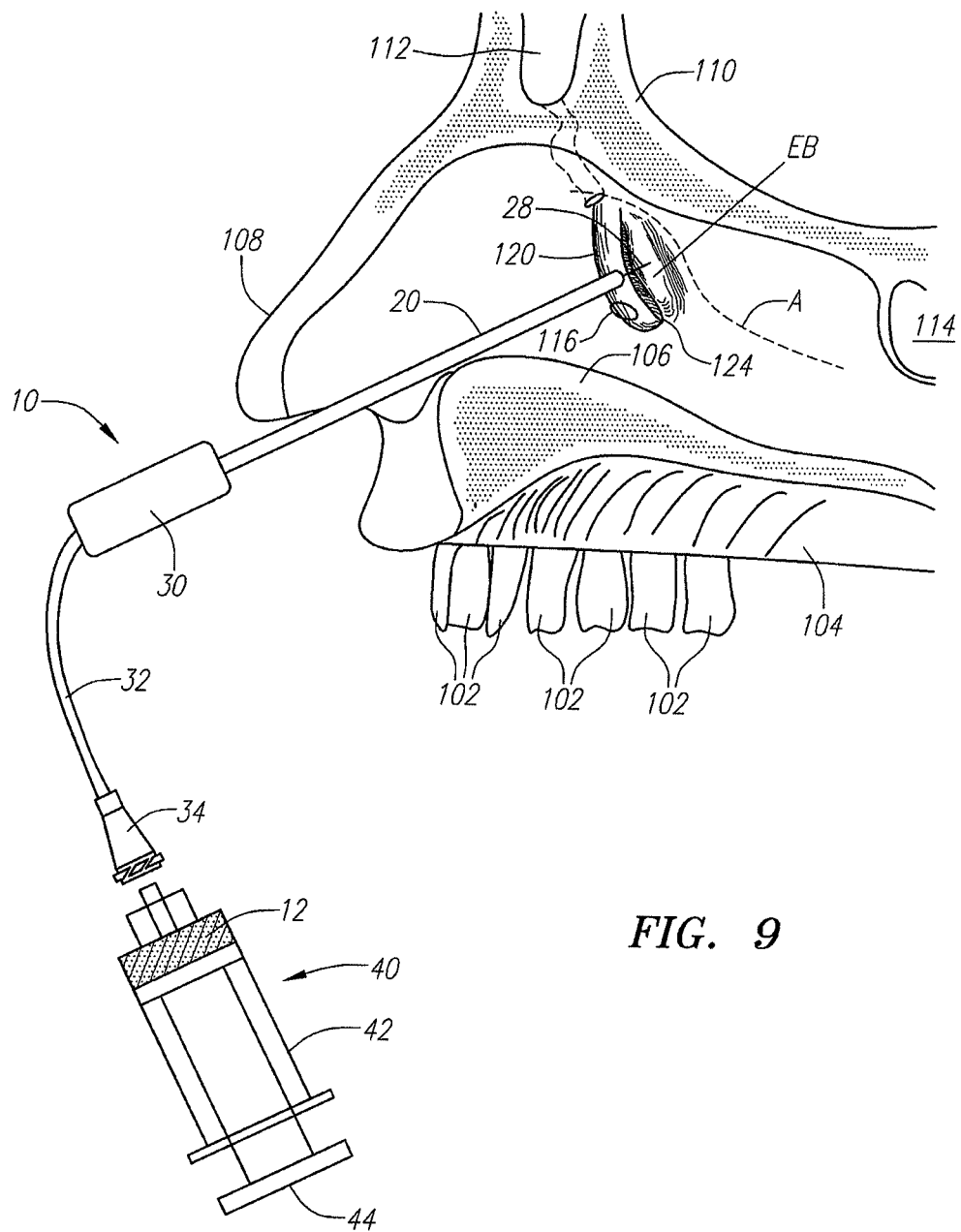
FIG. 9 illustrates the placement of an injection device into an ethmoid air cell via a transnasal approach.

FIG. 9 illustrates placement of an injection device 10 of the type illustrated in FIG. 1 via a transnasal route to treat an ethmoid air cell 18 such as the ethmoid bulla EB. In a transnasal approach, the injection device 10 preferably includes a relatively stiff elongate member 20. The stiff nature of the elongate member 20 aids in lightly displacing nasal structures such as the uncinate process 120 and/or middle turbinate 118 to place the sharpened needle 28 into the ethmoid bulla EB. The injection device 10 may be advanced with the aid of an optional visualization tool 80 such as an endoscope (not shown in FIG. 9). Once the delivery needle 28 is positioned near or adjacent to the ethmoid air cell 18, the delivery needle 28 is advanced across the wall of the ethmoid air cell 18 such that at least a portion of the delivery needle 28 lies within the interior of the ethmoid air cell 18.

With the delivery needle 28 within the ethmoid air cell 18, the therapeutic agent 12 may then be injected into the ethmoid air cell 18. For example, a dispensing device 40 such as a syringe may be coupled to the proximal hub 34 of the delivery device 10. The physician or other user may then depress the plunger 44 to forcibly transfer the therapeutic agent 12 from the syringe 40 and into the lumen 26 of the elongate member 20 and then into the interior space of the ethmoid air cell 18.

Figure 10:
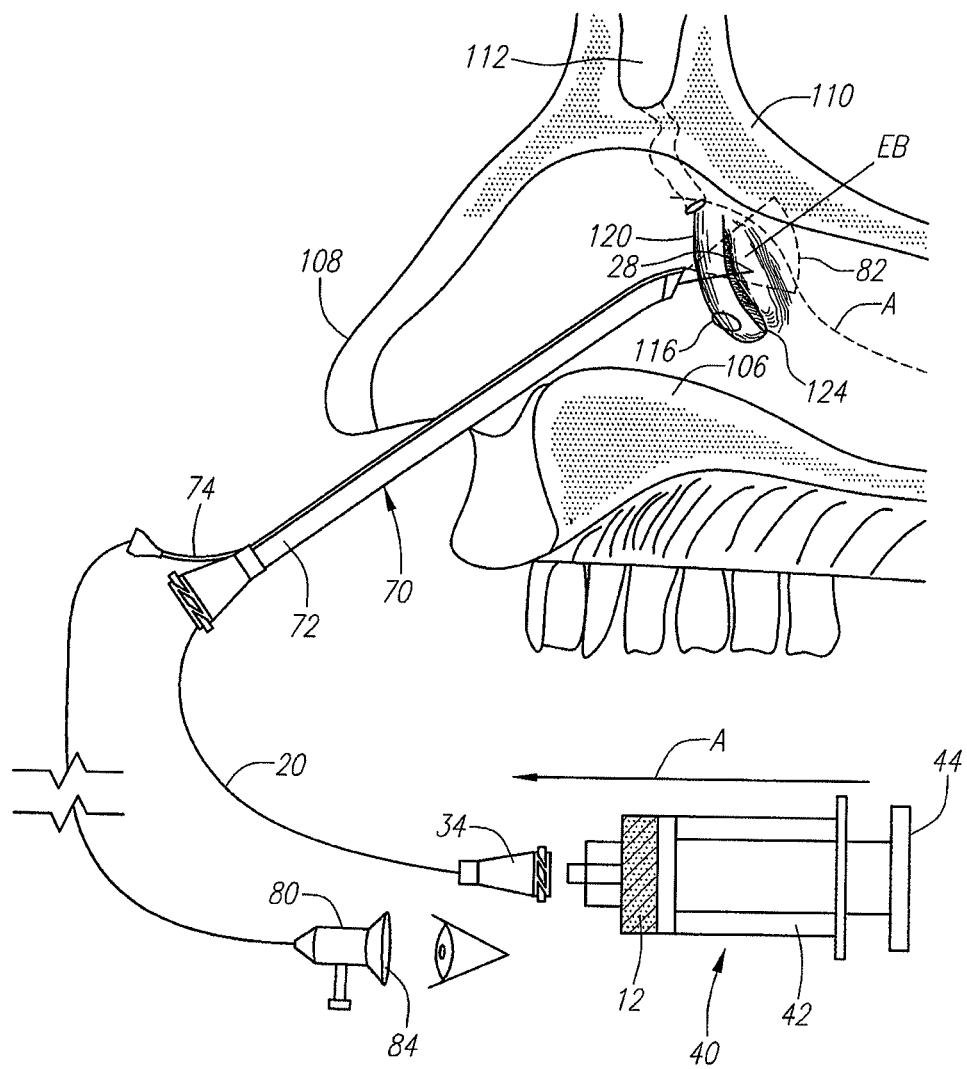
FIG. 10 illustrates the placement of an injection device according to another embodiment into an ethmoid air cell via a transnasal approach.

FIG. 10 illustrates placement of an injection device 10 of the type illustrated in FIG. 3 via a transnasal route to treat an ethmoid air cell 18 such as the ethmoid bulla EB. In this embodiment, the cannula 70 with the dual lumens 72, 74 is advanced transnasally to position a distal end towards the ethmoid bulla EB. An elongate member 20 such as a needle of the type described herein is advanced via a first lumen 72 while a visualization tool 80 such as an endoscope is advanced via the second lumen 74. In one aspect of the invention, the endoscope 80 may be pre-positioned within the second lumen 74 in order to guide the positioning of the cannula 70 relative to the ethmoid bulla EB. Once the cannula 70 is positioned properly, the elongate member 20 is advanced to penetrate the ethmoid air cell 18. Once inside, therapeutic agent 12 may be delivered using, for example, the dispensing device 40 operatively coupled to the elongate member 20.

Figure 11:
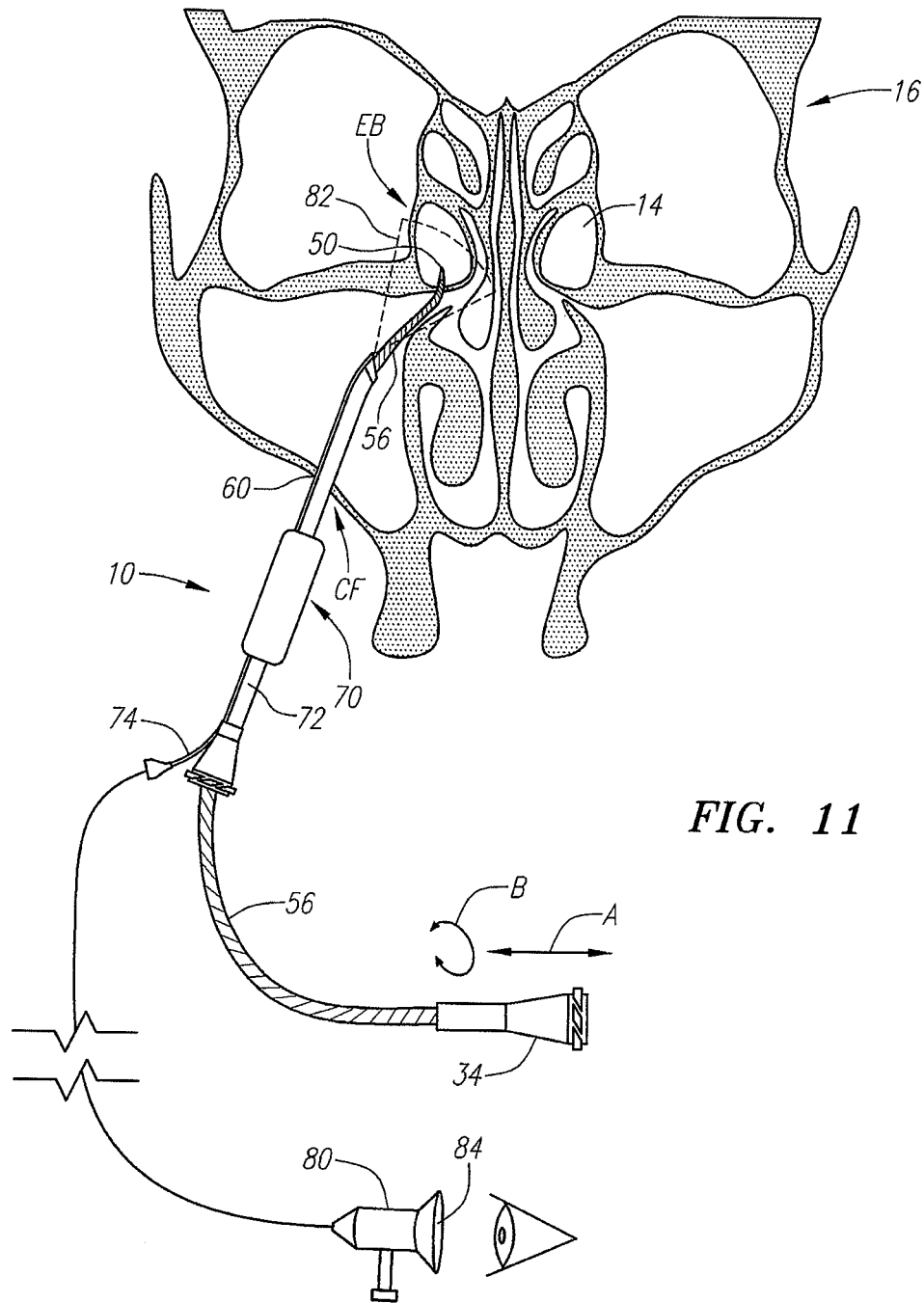
FIG. 11 illustrates the placement of an injection device according to another embodiment into an ethmoid air cell via a passageway or access site formed in the canine fossa region of the patient.

FIG. 11 illustrates placement of an injection device 10 of the type illustrated in FIGS. 5A-5C via an access passageway 60 formed in the canine fossa CF to treat an ethmoid air cell 18 such as the ethmoid bulla EB. The injection device 10, which may be a drilling device, is advanced through a lumen 72 of the cannula 70 that is inserted within a passageway 60 formed in the canine fossa CF region of the patient 16. A visualization tool 80 such as an endoscope is positioned within the second lumen 74 and is used to aid in positioning the injection device 10. As seen in FIG. 11, the drilling device 10 may be moved in the proximal and distal directions represented by arrow A. Also, the drilling device 10 may be rotated about its axis as represented by arrow B. The drilling device 10 may include a central lumen 26 there which may be used to deliver the therapeutic agent 12. In an alternative embodiment of the invention, however, the drilling device 10 may be solid. In this case, after the hole or passageway has been formed in the ethmoid air cell 18, the drilling device 10 would be withdrawn and an elongate member 20 such as a needle may then be advanced through the cannula 70 to deliver the therapeutic agent 12 within the interior of the ethmoid air cell 18.

While FIG. 11 illustrates a drilling device 10 that is positioned via a passageway 60 formed in the canine fossa CF region, it should be understood that the drilling device 10 may also be advanced and positioned via a transnasal approach.

Figure 12:
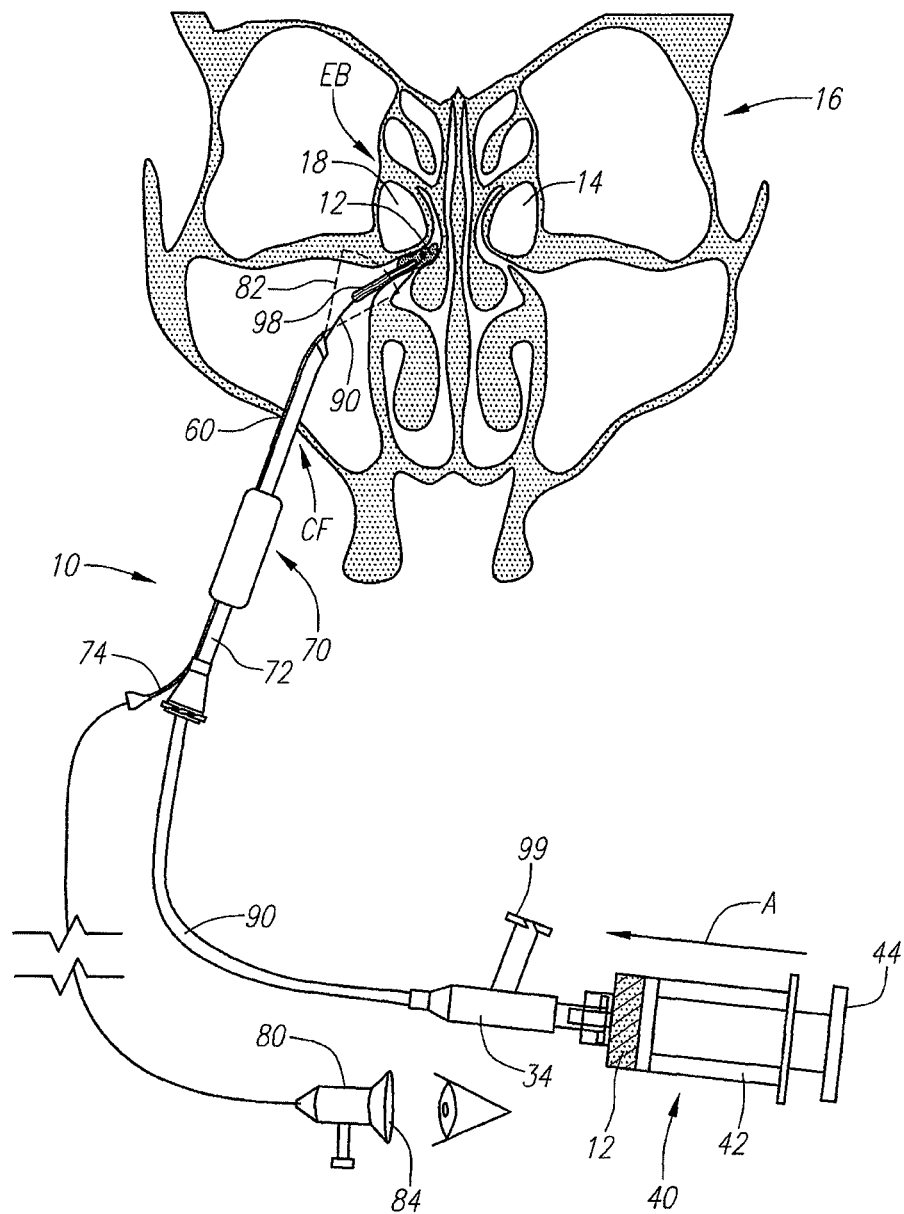
FIG. 12 illustrates the placement of an injection device according to another embodiment adjacent to an ethmoid air cell via a passageway or access site formed in the canine fossa region of the patient.

FIG. 12 illustrates an embodiment of a delivery device 90 like that illustrated in FIG. 6 that is used to delivery a therapeutic agent 12 on an exterior surface of an ethmoid air cell 18 like the ethmoid bulla EB. As seen in FIG. 12, the delivery device 90 is advanced through a lumen 72 of a cannula 70 that is positioned within an artificial passageway 60 formed in the canine fossa CF. The delivery device 90 includes an inflatable balloon 98 that can be used, for instance, to dilate the maxillary sinus ostium 116 and infundibulum 121. The inflatable balloon 98 may be inflated by pumping fluid into a proximally located hub 34 that includes an inflation port 99. In one preferred method, after the maxillary sinus ostium 116 and infundibulum 121 have been dilated, the balloon 98 is deflated. A lumen 100 extending through the delivery device 90 is used to delivery the therapeutic agent 12 onto an external surface of an ethmoid air cell 18 like the ethmoid bulla EB.

As seen in FIG. 12, therapeutic agent 12 may be delivered by depressing the plunger 44 of dispensing device 40 in the direction of arrow A. Therapeutic agent 12 then exits the distal end of the delivery device 90 and effuses onto the target site of interest. The delivery device 90 may be advanced distally or withdrawn proximally to facilitate delivery of the therapeutic agent 12 over an elongated target site. Because the therapeutic agent 12 in this case is not within the interior of the ethmoid air cell 12, it is preferable that the therapeutic agent 12 be relatively viscous and relatively slow to be absorbed. For example, Kenalog® is available as a cream, which may stay in place longer than a less viscous therapeutic agent. Furthermore, the addition of a vasoconstrictive agent may allow the agent to remain within the tissue even longer. It is also contemplated that in addition to the external delivery of therapeutic agent 12, delivery of the same or different therapeutic agent 12 to the interior of the ethmoid air cell 18 could be performed in conjunction using any of the above mentioned techniques or devices.

Figure 13:
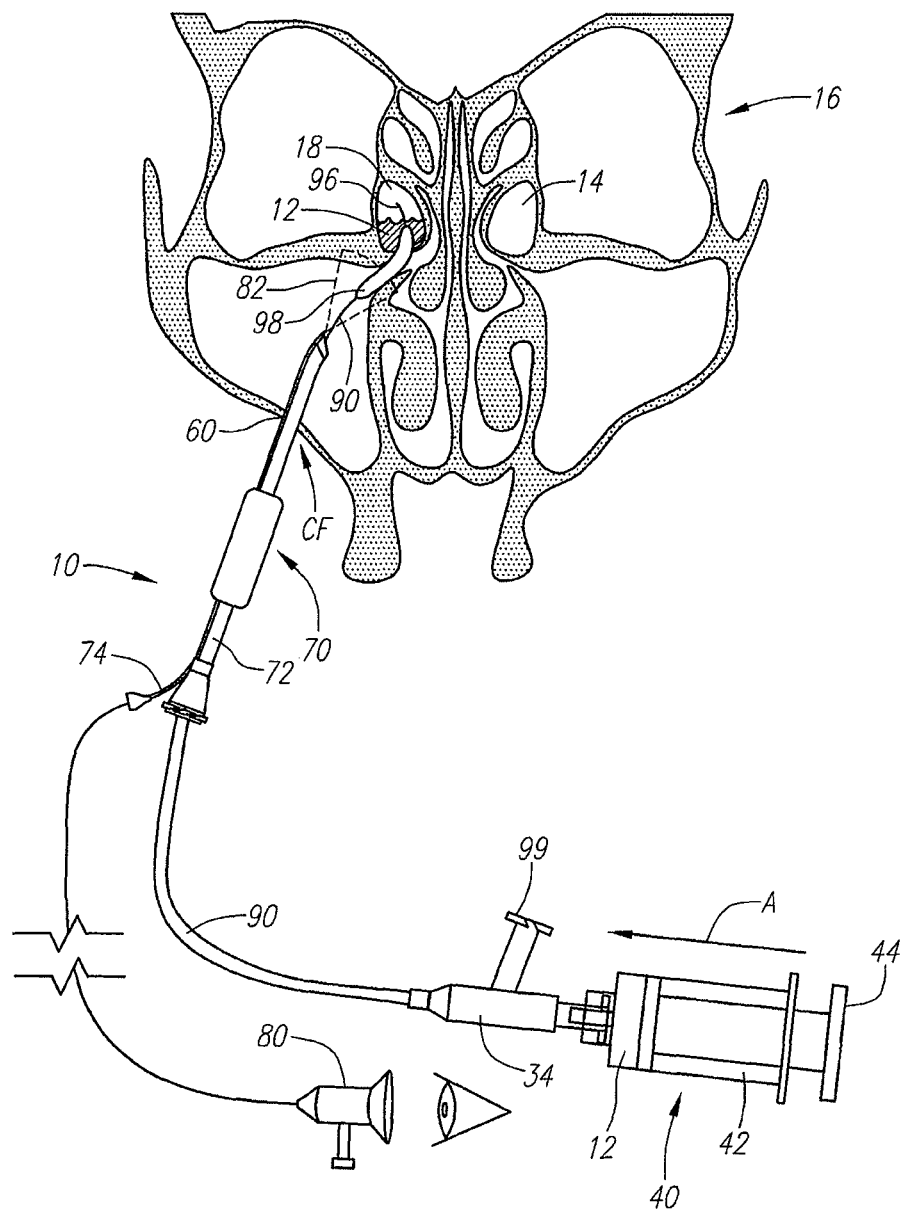
FIG. 13 illustrates the placement of an injection device according to another embodiment into an ethmoid air cell via a passageway or access site formed in the canine fossa region of the patient.

In an alternative embodiment as shown in FIG. 13, the delivery device 90 is similar to delivery device 90 shown in FIG. 6. In this embodiment, however, rather than a relatively blunt tip 96, delivery device 90 has a tip 96 that is sharp, similar to the needle 28 of the device 10 illustrated in FIG. 2. Referring again to FIG. 13, the sharpened tip 96 of delivery device 90 can be advanced across the wall of an ethmoid air cell 18, such as the ethmoid bulla EB. Then, with continued advancement of delivery device 90, the balloon portion 98 can be advanced across the wall of the ethmoid air cell 18. The balloon 98 can be inflated, to create an enlarged opening in the wall of the ethmoid air cell 18. A therapeutic agent 12 can then be infused (either simultaneously or stepwise) into the interior of the ethmoid air cell 18 in a manner similar to that described in connection with device 10 of, for example, FIG. 2. Delivery device 90 can be utilized either with a canine fossa approach, or a transnasal approach. If the delivery device 90 is positioned via the canine fossa CF, the balloon dilation may also concurrently dilate the maxillary ostium and infundibulum. However, the maxillary ostium and infundibulum may be dilated in a prior or subsequent step.

While embodiments of the present invention have been shown and described, various modifications may be made without departing from the scope of the present invention. The invention, therefore, should not be limited, except to the following claims, and their equivalents.

What is claimed is:

1. A method of treating diseased sinuses in a patient with a therapeutic agent comprising:
   providing an injection device comprising an elongate member having a distal region containing a balloon and a sharpened distal tip extending distally with respect to the balloon, and a proximal end, the proximal end being operatively coupled to a syringe containing a source of the therapeutic agent, the therapeutic agent consists of a fluid or fluid-like substance;
   inserting the sharpened distal tip of the injection device within an interior portion of an ethmoid air cell so that the balloon extends across a wall of the ethmoid air cell;
   dilating the balloon while the balloon extends across the wall of the ethmoid air cell;
   injecting the therapeutic agent into the interior portion of the ethmoid air cell using the syringe, the therapeutic agent being delivered while the sharpened distal tip of the injection device remains within the interior portion of the ethmoid air cell.

2. The method of claim 1, wherein the insertion of the injection device is accomplished transnasally.

3. The method of claim 1, wherein the therapeutic agent is injected prior to advancing a balloon catheter.

4. The method of claim 1, wherein the ethmoid air cell comprises an ethmoid bulla.

5. The method of claim 1, wherein the therapeutic agent is selected from the group consisting of an inflammation agent, an antibiotic, an anti-viral agent, an anti-fungal agent, a mucosal agent, an expectorant, a secretagogue, and a scarring agent.

6. The method of claim 1, wherein the injection device is removed during an episode of care.

\* \* \* \* \*